United States Patent
Mordon et al.

(10) Patent No.: US 6,582,421 B1
(45) Date of Patent: Jun. 24, 2003

(54) LASER PHOTOCOAGULATOR WITH FLUENCE ADAPTATION

(75) Inventors: Serge Mordon, Villeneuve-d'Asq (FR); Thomas Desmettre, Mons-en-Baroeul (FR)

(73) Assignees: Universite de Lille 2, Lille (FR); Centre Hospitalier Regional et Universitaire de Lille, Lille Cedex (FR)

( * ) Notice: Subject to any disclaimer, the term of this patent is extended or adjusted under 35 U.S.C. 154(b) by 0 days.

(21) Appl. No.: 10/030,548

(22) PCT Filed: Jul. 13, 2000

(86) PCT No.: PCT/FR00/02038

§ 371 (c)(1),
(2), (4) Date: Mar. 8, 2002

(87) PCT Pub. No.: WO01/03772

PCT Pub. Date: Jan. 18, 2001

(30) Foreign Application Priority Data

Jul. 13, 1999 (FR) .............................. 99 09112

(51) Int. Cl.[7] ................................................ A61B 18/18
(52) U.S. Cl. .................. 606/3; 606/9; 607/89
(58) Field of Search ............................. 606/3.9; 607/89

(56) References Cited

U.S. PATENT DOCUMENTS 5,576,013 A * 11/1996 Williams et al. ............ 424/423
5,658,323 A * 8/1997 Miller ......................... 607/89

* cited by examiner

*Primary Examiner*—Roy D. Gibson
*Assistant Examiner*—Henry M. Johnson, III
(74) *Attorney, Agent, or Firm*—Larson & Taylor, PLC

(57) ABSTRACT

The invention concerns a laser photocoagulator comprising a laser emitting at a wavelength within the ICG absorption spectrum and provided with focusing means and a programmed or controlled module powering the laser such that the mean fluence (F) at the focus starting from an initial time varies according to an increasing function in time not varying at any time by more than 10% of an increasing monoexponential corresponding to formula $F=F_0(1-e^{-t/\tau})$ wherein F is the initial fluence and $\tau$ is a time constant ranging between 3 and 5 mn.

10 Claims, 1 Drawing Sheet

LASER PHOTOCOAGULATOR WITH FLUENCE ADAPTATION

The invention relates to apparatus and methods for photocoagulating tissue, reinforced by administering a chromophore; in general, the chromophore is indocyanine green (ICG) which has an absorption peak in blood at 800 nanometers (nm) and lying in the range 760 nm to 840 nm as a function of dosage. This is the wavelength at which presently-available diode lasers emit.

Such methods have already been proposed for destroying neo vessels (new blood vessels) under the retina (article by David R. Guyer et al. "Indocyanine green angiography and dye-enhanced diode laser photocoagulation", Seminars in Ophthalmology, Vol. 7, No. 3, 1992) and in dermatology for photocoagulating cutaneous angiodysplasias situated at depth and difficult to access for treatment by lasers emitting in the absorption spectrum of hemoglobin.

The use of ICG for photocoagulation nevertheless encounters numerous difficulties, of which the main difficulty is its short lifetime in plasma, to which there can be added its progressive diffusion away from the new vessels into which it has been injected. The use of continuous injection for compensating short lifetime reduces selectivity because of the diffusion.

The invention seeks to reduce the consequences of short lifetime by using the observation that the dynamics of ICG elimination can be modelled with an approximation that is satisfactory for a period of about 10 minutes after administration in the form of a decreasing mono-exponential function having a time constant that lies in practice in the range 3 minutes (min) to 5 min.

Consequently, the invention proposes a laser photocoagulator comprising:
  a laser emitting at a wavelength lying in the absorption spectrum of ICG and provided with focusing means; and
  a laser power supply module programmed or controlled so that the mean flux density F at the focus starting from an initial instant varies as an increasing function of time that never departs by more than 10% from an increasing mono-exponential having the form $F=F_0(1-e^{-t/\tau})$ where F is the initial flux density and $\tau$ is a time constant lying in the range 3 min to 5 min.

Time t is measured from the administration of ICG and not from the beginning of laser treatment. $F_0$ is selected to have a value that is as high as possible within the limit set by ensuring selectivity of action on the vessels that have received the ICG. The present initial $F_0$ is selected as a function of the injected dose of ICG and of the time interval that elapses between injection and the first laser shot on the vessels. In practice, the injected dose of ICG will not exceed about 15 milligrams per kilogram (mg/kg) of tissue. The corresponding initial flux density is a decreasing and substantially linear function of dose starting from an initial value, for a zero dose, of the order of 300 joules per square centimeter ($J/cm^2$) for a zero dose.

Varying fluence (flux density) over time makes it possible to cause reproducible thermal damage to occur from one operation to another and to conserve selective photocoagulation of those vessels which have received ICG, providing that not more than about 10 minutes is allowed to elapse from injection.

The administered power, and thus the fluence, is adjusted by acting on an available parameter of the laser used. In the common case of a pulse laser, the modulus is programmed or controlled to cause the flux density to vary by modifying unit power and/or duration. The frequency of successive shots in a sequence can also be adjustable.

For example, it can be stated that a diode laser emitting at 810 nm and delivering a power of 0.8 watts (W) with pulses being applied over a period of up to 10 seconds (s) during which flux density can be varied from 60 $J/cm^2$ to 360 $J/cm^2$ gives good results when destroying vessels in the dermis.

Ordinary laser photocoagulators generally have an external connector enabling duration, spacing, and power of pulses to be controlled from an external control module. Such a module can include, in particular, a processor having a memory containing a program that determines how the power delivered by the laser photocoagulator should vary over time. The invention also provides such a control module programmed so as to cause flux density to vary in application of the above-defined function, and a program which, when loaded into a control module, causes said function to be executed.

In a variant embodiment of the invention, the photocoagulator device is associated with means that continuously supply an estimate of the concentration of ICG in the blood, and it is programmed in such a manner as to adjust mean flux density continuously as a function of the estimate so as to achieve compensation. The concentration estimating means can be used for continuously adjusting flux density by correcting the law stored in the power supply module. These means can also replace the stored relationship. Finally, they can be used for adjusting the time constant $\tau$.

By way of example, these means can be constituted by apparatus for measuring ICG concentration and sold under the name "ICG Clearance Meter" by Daiichi Pharmaceutical Co., where the estimate of concentration is based on the absorption of infrared light by the terminal phalaux of a finger. Such apparatus is used at present only for determining the rate at which ICG is eliminated by the liver and thus for evaluating possible deterioration of liver function.

It is also important to observe that the problem to be solved is associated with the rapid rate of decrease in the concentration in the blood of a chromophore, in particular ICG, that is injected to enable photocoagulation by thermal action, and is not associated with the fact tumor cells eliminate a photosensitizing agent more quickly than healthy cells during laser treatment of a cancer.

The above characteristics and others will appear more clearly on reading the following description of a particular embodiment, given as a non-limiting example. The description refers to the accompanying drawing, in which.

Figure 1:
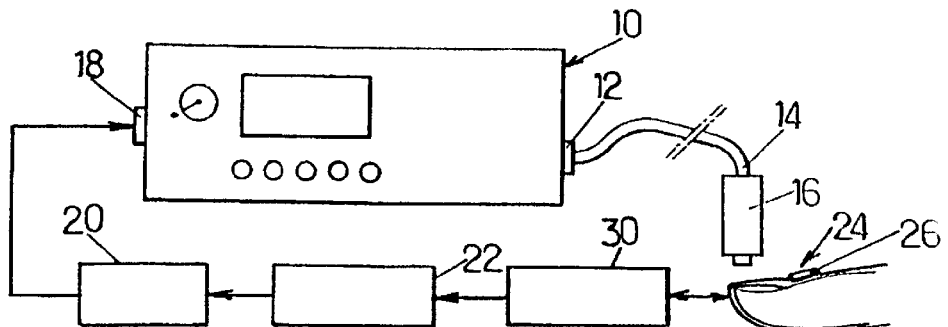
FIG. 1 is a diagram showing the various components of a photocoagulator which can be used for implementing the invention.

The photocoagulator whose general structure is shown by way of example in FIG. 1 comprises an assembly 10 containing a laser diode and its power supply module in a housing having a front panel provided with control buttons and indicators making it possible to adjust emitted power, the duration of each shot, and the interval between shots. The assembly shown is provided with a connector 12 for receiving an optical fiber 14 for conveying light power to an applicator 16. In addition, the housing of the assembly 10 is provided with a connector 18 for connection to an external control module comprising a host processor 22 and an interface 20. In general an RS232 serial link is used. This link enables the processor 22 to control the power and the duration of the or each pulse. The or each shot can be triggered by an operator, e.g. using a foot control. In the frequent circumstance where pulse power is determined by a voltage control, the control voltage can be generated by the interface 20.

It is possible in particular for the laser used to be the apparatus sold under the reference OPC-H005-FCTS which enables light output power to be adjusted over the range 0 to 5 W in steps of 0.1 W, which enables pulse width to be adjusted over the range 200 microseconds ($\mu s$) to 100 s, and which enables the spacing between pulses to be adjusted over the range 200 $\mu s$ to 100 s, with output at a wavelength of 808 nm.

The program for varying power output and pulse duration as a function of elapsed time is loaded into the processor 22. This program can make use of a table matching duration and pulse power with time elapsed since an initialization instant which corresponds to ICG being injected. The program can also be designed to calculate a polynomial function whose coefficients are loaded initially, with power duration then being calculated in real time each time a pulse is triggered.

Figure 2:
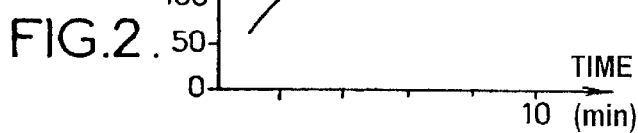
FIG. 2 shows an example of how flux density varies as a function of time from injection of ICG, for elimination dynamics modelled using a decreasing mono-exponential function with a time constant $\tau$ of 4.8 min.

By way of example, FIG. 2 shows theoretical variation to be given to flux density as a function of the time that has elapsed since injection, for a time constant $\tau$ of 4.8 min, after injecting a dose of 15 mg/kg of ICG, and for maximum flux density at the end of photocoagulation of 300 J/cm$^2$. An increase in dose of ICG would make it possible to increase the duration during which reinforced photocoagulation can be obtained.

For the relationship giving variation of the term $y=e^{-t/\tau}$, it is possible in particular to select the following relationship:

| Time (min) | y = exp (−x/4.8) or y = exp (−0.2083x) |
|---|---|
| 0 | 1.000 |
| 0.33 | 0.934 |
| 0.5 | 0.901 |
| 0.66 | 0.872 |
| 1 | 0.812 |
| 1.5 | 0.732 |
| 2 | 0.659 |
| 2.5 | 0.594 |
| 3 | 0.535 |
| 4 | 0.435 |
| 5 | 0.353 |
| 6 | 0.287 |
| 7 | 0.233 |
| 8 | 0.189 |
| 9 | 0.153 |
| 10 | 0.125 |

As mentioned above, the exponential can be simulated by a polynomial formula. The table below gives both a first degree polynomial and a second degree polynomial. It can be seen that the simple or first degree polynomial suffices to reduce error relative to the exponential to less than 10% as from 0.33 min to beyond 9 min. A second degree polynomial enables error to be reduced to less than 2% over the same range. An even smaller error could be obtained using a third degree formula.

| Time (min) | y = −0.0886x + 0.8857 | % error relative to exponential | y = 0.0086x$^2$ − 0.1693x + 0.9789 | % error relative to exponential |
|---|---|---|---|---|
| 0 | 0.886 | 11.4 | 0.979 | 2.1 |
| 0.33 | 0.856 | 7.7 | 0.924 | 1.0 |
| 0.5 | 0.841 | 6.0 | 0.896 | 0.5 |
| 0.66 | 0.824 | 4.4 | 0.871 | 0.1 |
| 1 | 0.797 | 1.5 | 0.818 | 0.6 |
| 1.5 | 0.753 | 2.1 | 0.744 | 1.3 |
| 2 | 0.709 | 4.9 | 0.675 | 1.5 |
| 2.5 | 0.664 | 7.0 | 0.609 | 1.5 |
| 3 | 0.620 | 8.5 | 0.548 | 1.3 |
| 4 | 0.531 | 9.7 | 0.439 | 0.5 |
| 5 | 0.443 | 9.0 | 0.347 | 0.5 |
| 6 | 0.354 | 6.8 | 0.273 | 1.4 |
| 7 | 0.266 | 3.3 | 0.215 | 1.7 |
| 8 | 0.177 | 1.2 | 0.175 | 1.4 |
| 9 | 0.088 | 6.5 | 0.152 | 0.2 |
| 10 | 0.000 | 12.5 | 0.146 | 2.1 |

In general, treatment is performed using a single pulse of duration and power selected so that the total flux density received by the tissue is that which is deduced from $F_0$ for the tissue concerned and for the time which has elapsed since injection. In practice, it is often necessary to select a pulse duration having a value that corresponds to three to five times the relaxation time of the vessels that are to be treated so as to allow heat to diffuse from the blood towards the vessel wall. The power to be delivered is deduced while taking account of the size of the spot and the time that has elapsed since ICG was administered.

The method implemented can include a preliminary step of determining the exact location of the vessels to be attacked by illuminating these tissues under low power after ICG has been administered. Fluorescence makes it possible to determine the location of the new vessels and can define the exact location to be given to the laser spot for coagulation purposes.

Figure 3:
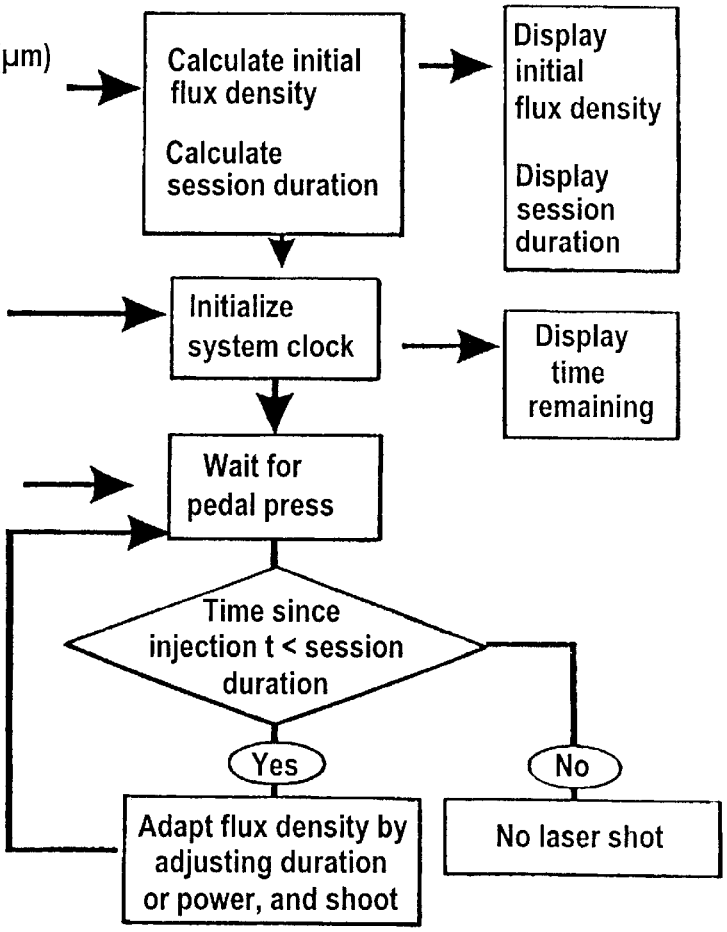
FIG. 3 is a flow chart for controlling a photocoagulator in a particular implementation.

FIG. 3 is a flow chart summarizing one possible implementation of the device when using a single shot. This flow chart is designed to stop shooting when the time that has elapsed since injection exceeds the full duration of a treatment session, including the duration of the laser pulse.

In a variant embodiment of the invention, the processor 22 receives a signal representative of ICG concentration in the blood from a measuring apparatus. The measuring apparatus has a pickup 24 designed to be fixed on a finger and having a light-emitting diode (LED) 26 which emits light in the absorption range of ICG, associated with a detector element such as a photodiode 28. A monitor 30 generates a signal representative of real concentration on the basis of measured absorption. The processor 22 is designed to control the energy of the treatment laser pulse by taking account of the signal output by the monitor, either in real time for controlling the dose that is to be applied, or to adjust the dose as a function of the received signal. This disposition makes it possible, e.g. on the basis of initial calibration, to take account in particular of any deterioration that may have occurred in the patient's liver function.

Instead of being performed on a finger, measurement can be also be performed on some other part of the body, e.g. on an earlobe.

The initial value $F_0$ of the fluence is selected in particular as a function of the dose of ICG that is injected. This dose will generally not exceed 1.5 mg/kg of patient body weight. $F_0$ is the flux density which produces coagulation of the vessels to be destroyed without damaging adjacent tissue at the initial concentration. In practice, it is common to use a flux density $F_0$ of about 20 J/cm² at maximum dosage, when treating new vessels at the back of the eye. The time at the end of which laser treatment is performed is the time required for ICG to invade the entire circulatory system after being injected intravenously. The duration of the laser emission will depend to a large extent on the location, the nature, and the diameter of the vessels to be treated. When treating the back of the eye, the duration is generally 10 ms to several tens of ms. For new vessels located in mucous membranes, the duration can be as long as 2 s, because diffusion towards adjacent tissue that is to be preserved is longer.

The applicator 16 can be placed outside the body or at the end of an endoscope when it is necessary to treat internal mucous membranes.

What is claimed is:

1. A laser photocoagulator comprising:

a laser having an emission wavelength lying in the absorption spectrum of ICG and provided with focusing means; and a laser power supply module controlling emission by said laser and arranged for causing a mean fluence F at a focus of said focussing means to vary, starting from a predetermined initial instant, as an increasing function of time that does not depart by more than 10% from an increasing mono-exponential having the form $F=F_0(1-e^{t/\tau})$ where $F_0$ is a predetermined value of the fluence, t is time elapsed and $\tau$ is a time constant lying in the range 3 min to 5 min.

2. A photocoagulator according to claim 1, wherein the power supply module is programmed and controlled to cause said fluence to vary by modifying power delivered by said laser.

3. A photocoagulator according to claim 1, wherein the power supply module is programmed and controlled to cause said fluence to vary by modifying a duration of a pulse delivered by said laser.

4. A photocoagulator according to claim 1, further comprising an external programmed unit controlling the power supply module.

5. A photocoagulator according to claim 1, wherein the increasing function is at least a second degree polynomial function.

6. A photocoagulator according to claim 1, wherein the increasing function is a linear function that is terminated if it deviates more than 10% from the mono-exponential function.

7. A photocoagulator according to claim 1, wherein the emission wavelength of the laser is in a range of 700 nm to 900 nm.

8. A photocoagulator according to claim 1, wherein the power supply module is connected to apparatus for measuring the instantaneous concentration of ICG in the blood and designed to take account of an output signal from said apparatus in order to adjust flux density.

9. A method of photocoagulating neo blood vessels of a patient, the method comprising the steps of:

administering a predetermined dose of indocyanine green to a patient; and after a length of time has elapsed after administration, focusing, on the neo vessels to be photocoagulated, a laser pulse that is controlled in such a manner that a mean fluence F of the laser pulse at the focus, varies from an initial flux density $F_0$ according to a law which does not depart by more than 10% from a value $F=F_0(1-e^{-t/\tau})$ where $F_0$ is a predetermined flux density, t is time elapsed after administration of said indocyanine green and $\tau$ is a time constant lying in the range 3 min to 5 min.

10. A method according to claim 9, wherein said predetermined flux density is 20 J/cm2.

* * * * *